United States Patent [19]

Dimmit et al.

[11] Patent Number: 4,578,250
[45] Date of Patent: Mar. 25, 1986

[54] METHOD FOR THE RECOVERY OF PALLADIUM

[75] Inventors: Jeffrey H. Dimmit, Williamsville; Michael Van Der Puy; David S. Soriano, both of Cheektowaga, all of N.Y.

[73] Assignee: Allied Corporation, Morris Township, Morris County, N.J.

[21] Appl. No.: 626,956

[22] Filed: Jul. 2, 1984

[51] Int. Cl.$^4$ .................................................. C01G 55/00
[52] U.S. Cl. .................................. 423/22; 75/101 BE
[58] Field of Search ........................ 423/22; 75/101 BE

[56] References Cited

U.S. PATENT DOCUMENTS

| | | | |
|---|---|---|---|
| 3,437,431 | 4/1969 | Platz et al. | 423/22 |
| 3,922,330 | 11/1975 | Pittie et al. | 423/22 |
| 3,967,956 | 7/1976 | Payne | 423/22 |
| 4,133,834 | 1/1979 | Pickens | 260/566 |
| 4,331,634 | 5/1982 | Shanton et al. | 423/22 |

FOREIGN PATENT DOCUMENTS

| | | | |
|---|---|---|---|
| 2459099 | 6/1975 | Fed. Rep. of Germany | 423/22 |
| 2518631 | 4/1976 | Fed. Rep. of Germany | |
| 2013644 | 8/1979 | United Kingdom | |
| 2104516 | 9/1983 | United Kingdom | |

OTHER PUBLICATIONS

M. J. Cleare, et al., J. Chem. Tech., Biotechnol., vol. 29 (1979) pp. 210–224.

Primary Examiner—Jack Cooper
Attorney, Agent, or Firm—Arthur J. Plantamura; Jay P. Friedenson

[57] ABSTRACT

The present invention is directed to a method of separating and purifying palladium which is present in a solution with at least one other platinum group metal by adjusting the pH of the solution to from about 0 to 5, contacting the acidified solution with an ortho alkoxy substituted phenyl oxime of the formula:

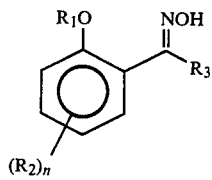

or a composition comprising of one or more of said compounds dissolved in an organic solvent, wherein:

n is an integer of from 1 to 4;

$R_1$ is alkyl, cycloalkyl, or aralkyl; and $R_2$ is nitro, halogen, hydrogen or substituted ro unsubstituted alkyl, alkoxy, aryloxy, cycloalkyl, aryl, aralkyl or alkaryl, wherein permissible substituents are those which are inert to process conditions; and $R_3$ is alkyl, aryl, alkaryl, cycloalkyl or aralkyl either unsubstituted or substituted with one or more of the above referenced permissible substituents, using solvent extractions techniques, separating the aqueous phase from the organic phase containing substantially all of the palladium in association with the oxime compound, and stripping the palladium from the association with the oxime compounds in the organic phase by extraction with an aqueous ammonia solution.

27 Claims, No Drawings

METHOD FOR THE RECOVERY OF PALLADIUM

BACKGROUND OF THE INVENTION

1. Field of Art

This invention relates to a method for the recovery and purification of palladium. More particularly, this invention relates to a novel method of recovering and purifying palladium through use of ortho alkoxy substituted phenyl oxime compounds which are capable of selectively separating and recovering palladium from aqueous compositions and mixtures containing palladium and other metal ions such as aluminum, nickel, iron, copper, platinum, rhodium, ruthenium and the like.

2. Prior Art

The recovery and purification of platinum group metals, such as palladium and platinum, are important commercial processes. Such processes are useful in the recovery of palladium from solutions obtained in the recovery of mineral deposits of the platinum metals which solutions commonly contain in addition to palladium, ruthenium, rhodium, iridium, platinum, aluminum, iron, and nickel. Such processes are also useful in the recovery of palladium from spent catalyst materials, such as materials obtained from automobile catalytic converters.

Several extraction methods have been developed for recovery of metal values. Solvent extraction processes for the recovery of metal values have certain well recognized advantages over other recovery methods, and such solvent extraction processes are increasing in number and types of applications. Fundamental to a successful solvent extraction process for the recovery of a platinum group metal such as palladium, is the identification of a water immiscible composition, (combination of compounds which will selectively bind to the metal and a solvent) which will selectively extract one platinum group metal from an aqueous solution containing the platinum group metal and other metals. A further requirement for a successful metals recovery by solvent extraction techniques is an extracting composition having the property such that metal values extracted by the extracting solvent can be recovered from same using another suitable aqueous phase.

Illustrative of such prior art solvent extraction methods are those described in U.S. Pat. No. 3,967,956 and United Kingdom Pat. No. 2,013,644. In the processes of these patents, palladium is recovered from a mixture of palladium and other platinum group metals through use of an extracting composition containing ortho hydroxy oxime compounds, such as alkyl substituted ortho-hydroxyphenyl oxime compounds. The extracted palladium metal is removed from the extracting composition by contacting same with a strong acid solution. This method is generally a useful procedure for recovering certain metals from the extracting composition because this recovery is pH dependent. With ortho-hydroxy phenyl oximes, the extraction process is dependent on the ionizable nature of the phenolic hydrogen, and in the $Cu^{+2}$ system is generally believed to follow the following equilibrium in which "LH" is the un-ionized oxime:

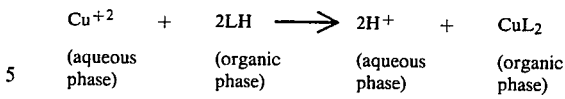

| | | | |
|---|---|---|---|
| $Cu^{+2}$ | + 2LH | $\longrightarrow$ 2H$^+$ | + $CuL_2$ |
| (aqueous phase) | (organic phase) | (aqueous phase) | (organic phase) |

Presumably, the $Pd^{+2}$ system would operate in a similar manner when being extracted by orthohydroxy phenyl oxime compounds. In which case palladium values are extracted into the organic, water immiscible extracting composition as the neutral species "$PdL_2$", while LH ionizes in the aqueous phase so that the acidity of the aqueous phase increases. Recovery by treatment with strong acid is effective because by shifting the equilibrium the oxime is protonated releasing the palladium as $Pd^{+2}$ which migrates to the aqueous phase.

SUMMARY OF THE INVENTION

In accordance with this invention, there is provided a novel method of selectively separating and recovering palladium from aqueous solution containing palladium and other metals such as platinum, aluminum, ruthenium, rhodium, iron, copper, nickel, and the like. The process of this invention comprises the steps of (a) adjusting the PH of a solution comprising palladium and at least one other metal to 5 or less (if necessary);

(b) contacting said acidic solution of step (a) with one or more oxime compounds of the formula:

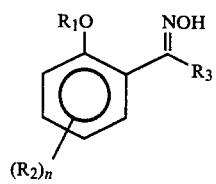

or a composition comprising of one or more of said compounds dissolved in an appropriate organic solvent, wherein:

n is an integer of from 1 to 4;

$R_1$ is alkyl, cycloalkyl, or aralkyl; and $R_2$ is nitro, halogen, hydrogen or substituted or unsubstituted alkyl, alkoxy, aryloxy, cycloalkyl, aryl, aralkyl or alkaryl, wherein permissible substituents are those which are inert to process conditions; and $R_3$ is alkyl, aryl, alkaryl, cycloalkyl or aralkyl either unsubstituted or substituted with one or more of the above referenced premissible substituents;

(c) removing from contact with said aqueous acidic solution the organic phase containing all or a part of palladium originally present in said solution and said oxime compound; and (d) extracting said palladium from said organic phase with an aqueous ammonia solution.

The novel process of this invention obviates many of the deficiencies of the prior art processes which use hydroxy substituted phenyl oxime compounds as the extractant. For example, through the use of the method of this invention palladium can be selectively extracted from aqueous solutions of palladium and other metals, including copper. Moreover, in the process of this invention, the palladium can be recovering from the organic phase merely by treatment with aqueous ammonia, and strong acids are not required.

DESCRIPTION OF THE PREFERRED EMBODIMENTS

The process of this invention includes four steps. In the first step of the process of this invention the pH of an aqueous solution comprising palladium and at least one other metal is adjusted to about 5 or less. Of course, if the pH of the solution already falls within this range, no adjustment is required. The source of the aqueous solution is not critical and can vary widely. For example, such solution can be obtained in the recovery of mineral deposits of the platinum family metals which may contain in addition to palladium, platinum, ruthenium, rhodium, aluminum, cobalt, lead, iron, copper, nickel and like metals. The solution can be obtained from process for recovery of palladium from spent palladium containing catalyst materials. Usually these solutions are obtained directly by the acidic digestion of the palladium containing catalytic material in which palladium is usually in association with inert support materials such as silica or alumina. Because of the acidic digestion no specific pH adjustment step is required. Such solutions can also be obtained by acidic digestion of materials in which palladium is present in conjunction with other materials as for example in an alloy, or simply associated with such metals in base metal parts. Here again, the pH of the solution resulting from the digestion step usually falls within the above-referenced range, and no additional pH adjustment is required.

The adjustment of the pH of the aqueous solution is preferrably carried out by addition thereto of an acid or base material usually in the form of an aqueous solution, depending on whether an increase or decrease in pH is desired. The type of acid or base material employed is not critical, and can be varied widely. Usually, the type of material employed will normally depend on the initial pH of the solution; and the desired final pH. Illustrative of useful acidic and basic materials, and preferred for use in the practice of this invention are strong mineral acids such as hydrochloric acid, sulfuric acid, and the like, and strong inorganic bases such as the alkali metal hydroxides such as sodium hydroxide, potassium hydroxide, and lithium hydroxide. Particularly preferred materials for adjusting the pH of the aqueous solution are hydrochloric acid and sodium hydroxide.

The pH of the aqueous solution is adjusted to about 5 or less. In the preferred embodiments of the invention, the pH is adjusted to from about −0.5 to about 5 and in the particularly preferred embodiments of the invention is adjusted to from about 0 to about 3. Amongst these particularly preferred embodiments, most preferred are those embodiments of the invention in which the pH of the aqueous solution is adjusted to from about 0 to about 1.

In the second step of the process of this invention, the solution is contacted with one or more compounds of the formula:

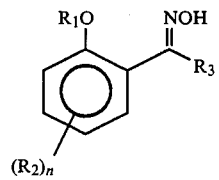

or a composition comprised of one or more of said compounds dissolved in an appropriate organic solvent, wherein n, $R_1$, $R_2$ and $R_3$ are as described above.

The following compounds are illustrative of compounds within the purview of the generic formula set forth above, which can be used in the process of this invention, all of which can be conveniently prepared by simply selecting appropriate reactants for use in the procedures described herein below:

(2-Methoxy-5-methyl)phenyl,nonyl ketoxime
(2-Methoxy-5-methyl)phenyl pentadecyl ketoxime
2-Methoxy-5-nonylbenzophenone oxime
2-Methoxy-5-heptadecylbenzaldoxime
2-Methoxy-5-nonyl-4'-methyl benzophenone oxime
[(2-Methoxy-5-(α,α-dimethylbenzyl)] phenyl hexyl ketoxime
(2-Ethoxy)phenyl pentadecyl ketoxime
2-Methoxy-4-phenyl benzophenone oxime
(2-Methoxy-4-chloro-5-methyl)phenyl pentadecyl ketoxime
2-Methoxy-3,5-dinonyl benzophenone oxime
2-Methoxy-3,5-dinonyl acetophenone oxime
2-Methoxy-5-nonyl-4'-chloro benzophenone oxime
2-Methoxy-5-(t-butyl)-3'-hexyl benzophenone oxime
2-Methoxy-4'-methyl benzophenone oxime
(2-Methoxy-5-nitro)phenyl 2'-napthyl ketoxime
2-Ethoxy-5-nonyl benzaldoxime
(2-Methoxy-4-methyl 4'-fluorobenzophenone oxime
(2-Methoxy-4-methyl)phenyl benzyl ketoxime
2-Methoxy-4'-phenyl benzophenone oxime
2,4-Dimethoxy-4'-methyl benzophenone oxime
(2-Ethoxy-4-phenoxy)phenyl propyl ketoxime Illustrative of suitable $R_1$ groups are alkyl such as methyl, ethyl, propyl, isopropyl, isobutyl, butyl, pentyl, hexyl, and heptyl; cycloalkyl such as cyclopropyl, cyclohexyl, cyclopentyl, cyclobutyl and the like; aralkyl such as benzyl, phenethyl, phenebutyl and the like.

Illustrative of useful $R_2$ substituents are methoxy, phenoxy, ethoxy, chloro, fluoro, hydrogen, phenyl and the above-referenced $R_1$ substituents. Exemplary of $R_3$ substituents are hydrogen; and the above described illustrative $R_1$ substituents. These $R_2$ and $R_3$ groups may be unsubstituted or substituted with one or more substituents which are inert to the process condition. Illustrative of such permissible substituents are alkyl, halogen, nitro, alkoxy, aryloxy, cycloalkyl and the like.

Preferred compounds for use in the process of this invention are those of the above-referenced generic formula in which n is 1 or 2, and $R_1$, $R_2$ and $R_3$ are as discribed above, with the provison that $R_2$ is substituted at the 4th and/or 5th positions on the phenyl ring. Particularly preferred compounds for use in the process of this invention are those of the above generic formula in which:

n is 1 or 2;

$R_1$ is straight chain alkyl having from 1 to about 6 carbon atoms; and $R_2$ and $R_3$ are the same or different and are unsubstituted alkyl, aralkyl, aryl or alkaryl with the proviso that the $R_2$ substituents are substituted at the 4th and/or 5th positions on the phenyl ring, and with the further proviso that $R_2$ and $R_3$ together contain a total of from about 15 to about 30 carbon atoms.

Amongst the particularly preferred compounds for use in the process of this invention most preferred for use are those of the aforementioned formula in which:

n is 1;

$R_1$ is straight chain alkyl having from 1 to 3 carbon atoms;

$R_2$ is straight chain alkyl having from 1 to about 12 carbon atoms, most preferably about 9 carbon atoms substituted at the 4th or 5th position on the phenyl ring; and $R_3$ is straight chain alkyl having from about 12 to about 25 carbon atoms, and aryl (most preferably phenyl).

Especially efficacious compounds for use in the process of this invention are those of the above formula in which $R_1$ is methyl, $R_2$ is straight chain alkyl having about 9 carbon atoms, and $R_3$ is phenyl; and those of the above formula in which $R_1$ and $R_2$ are methyl and $R_3$ is straight chain alkyl having from about 12 to about 25 carbon atoms. Of these compounds, experimentation has shown that (2-methoxy-5-methyl)phenyl pentadecyl ketoxime and 2-methoxy-5-nonylbenzophenone oxime exhibit outstanding efficacy.

The compounds for use in the process of this invention can be conveniently prepared by a variety of methods. One preferred method for preparing such compounds is illustrated in the following Reaction Scheme A.

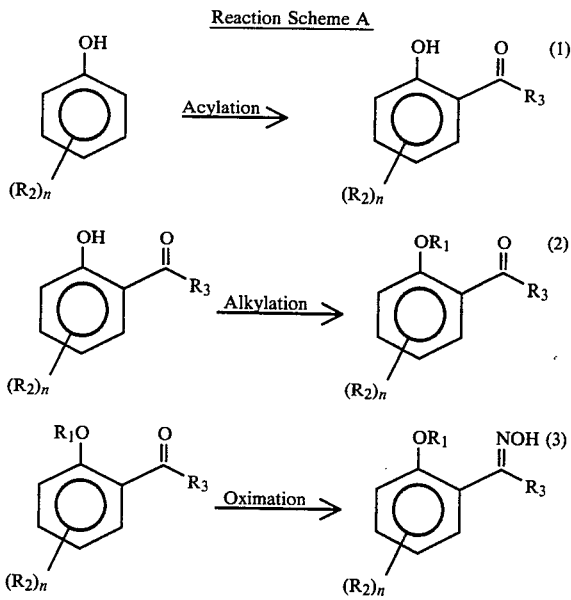

Reaction Scheme A wherein n, $R_1$, $R_2$ and $R_3$ are described above.

In the first step of the process, an appropriately substituted phenol is acylated using conventional acylation techniques to give the corresponding phenol containing an ortho substituted acyl group. The acylation of substituted phenols may be accomplished by several techniques. One method which can be used to prepare the acylated phenol utilizes the condensation of phenol with a benzotrichloride catalyzed by aluminum chloride described by M. S. Newman and A. G. Pinkus (*J. Org. Chem.*, 1954, 19, 985-1002). Another method which can be employed is the condensation of a phenol with a carboxylic acid using boron trifluoride as a catalyst, as described by N. P. Buu-Hoi and J. Seailles (*J. Org. Chem.*, 1955, 20, 606). The reaction may be conducted without a solvent, as the reaction mixtures are generally fluid at typical reaction temperatures of 75°-150° C. Alternatively, aprotic inert solvents such as trichloroethylene or carbon tetrachloride may be used as a solvent.

Generally, when boron trifluoride is used as a catalyst gaseous boron trifluoride is bubbled subsurface into the reaction mixture at atmospheric pressure. Other equivalent procedures, such as the use of an autoclave, are apparent to those skilled in the art. Good yields of acylated product are obtained when the phenol or substituted phenol is present in excess (1.2-1.6 molar equivalents) in order to insure monoacylation. Preferably, a para-substituted phenol is also used to insure ortho-acylation. Para-acylation yields material which does not selectively form a complex with divalent palladium and which generally is less stable under the use conditions.

Separation of the product acylated phenol from the starting phenol will usually depend on the substitutent on the phenol and the acyl group, and on other factors known to those of skill in the art; and must therefore be determined on a case by case basis through use of known scientific principles. For example when p-cresol is used as the substituted phenol, and the acyl group contains a long hydrocarbon chain, the product can be separated from the starting material by processing the reaction mixture into methanol. p-Cresol is soluble in methanol whereas the desired product is insoluble.

The temperature required for the acylation depends to a large degree on the catalyst used and to other factors known to those of skill in the art. For example, when boron trifluoride is used as the catalyst the reaction rate increases with increasing temperature until a temperature is reached such that gaseous boron trifluoride boils out of the reaction flask when the reaction is conducted at atmospheric pressure. Thus, a temperature of from about 120° to about 130° C. seems to be the optimum for carrying out the acylations under these conditions.

In the second step of the process, the phenolic group is alkylated with an appropriate alkylating agent such as an alkyl halide or dimethyl sulfate. A number of techniques are also useful for the alkylation or arylation of the phenolic group. For some phenols, procedures typical of alkyl aryl ether syntheses may be employed, e.g., ethanolic NaOH and an alkylating agent such as dimethylsulfate, or potassium carbonate in acetone containing an alkyl iodide. Such procedures are exemplified in the literature by G. N. Vyas and N. M. Shah (*Org. Synthesis Coll. Vol.* 4, 836 (1963).

Other alkylation methods which involve the phase-transfer catalyzed alkylation of the phenol can also be employed. For example, an aqueous phase containing a suitable base such as sodium hydroxide, and a phase transfer catalyst such as tetra-n-butylammonium bromide can be contacted with a water-immiscible organic solvent such as methylene chloride containing the dissolved phenol and an alkylating agent such as methyl iodide. In the phase transfer reaction there is considerable flexibility in the choice of base used, the phase transfer catalyst, the organic solvent and the alkylating agent. The base can be an alkali metal hydroxide or carbonate, i.e. bases which are alkaline enough to ionize the acylated phenol. The base is used in at least a stoichiometric amount relative to the phenol. The phase transfer catalyst is usually a quaternary alkyl ammonium halide or hydroxide, and can be used in less than stoichiometric amounts (e.g. 0.01 to 0.1 equivalents). The important feature of the phase transfer catalyst is that, with hydroxide as the counterion, it has substantial solubility in the organic solvent. Alternatively, crown ethers can be employed as the phase transfer catalyst, but are generally more expensive. The organic solvent should be immiscible with water and should readily dissolve the acylated phenol. Suitable solvents are the chlorinated methanes and ethanes and aromatic hydrocarbons solvents such as toluene and benzene.

Alkylation reactions under phase transfer conditions are commonly performed at a temperature of of from about 0° C. to about 40° C. The upper temperature is limited by the boiling point of the aqueous or organic phase, whichever is lower.

Finally in the third step of the process, the carbonyl portion of the compound is oximated with a conventional oximation agent, such as hydroxylamine. The oximation of the carbonyl compound can be carried out by treating the compound with hydroxylamine in an alcohol solvent such as ethanol or methanol at reflux for 2–3 hours. A typical procedure from the literature is that described by A. Lachman, Org. Syn, Coll, Vol. 2, 70 (1943).

For the oximation of the aryl alkyl ketones, preferably a slight excess (1.05-1.15 equivalents) of an hydroxylamine salt (the hydrochloride or sulfate) is neutralized with sodium hydroxide, or sodium or potassium carbonate in aqueous solution or in a water-alcohol co-solvent. If a co-solvent is used which has relatively low water content, the neutralization byproduct, e.g. sodium chloride, will not be soluble and can be filtered, if desired. The ketone, dissolved in alcohol is then added. The reaction mixture is refluxed 1–2 h during which time additional alcohol can be added to maintain homogeniety. On cooling the reaction mixture, the product oxime will often separate as a solid or an oil. Otherwise, the volatile alcohol solvent can be removed and the residue washed with water providing the solid or liquid oxime.

The oxime compound can be used neat, if liquid at the operating temperature, or, alternatively can be dissolved in an appropriate solvent. As used herein an "appropriate solvent" is any solvent which is substantially water immiscible, has a boiling point higher than the highest temperature employed in the process at the operating pressure, is inert under the process conditions and is capable of dissolving at least about 2% of an oxime compound or a mixture of such compounds based on the total weight of the solution. Illustrative of useful solvents are aromatic, aliphatic and cycloaliphatic hydrocarbons such as toluene, cyclohexane, xylenes, chlorinated hydrocarbons, kerosenes such as the Escaid ® series marketed by Exxon, or commercial blends of high boiling materials (aliphatic and aromatic) such as Fisher Brand K-10 or Shell Solvent 460. The preferred solvent is kerosene.

In the preferred embodiments of the invention, the aqueous solution containing palladium and other metals is contacted with a solution of one or more of the oxime compounds dissolved in an appropriate solvent. In general, the concentration of the oxime compound in said solution is at least about 2% by weight of the solution. In the preferred embodiments of the invention, the concentration of the oxime compound in said solution is from about 2 to about 50% by weight of the solution, and in the particularly preferred embodiments is from about 5 to about 25 weight % on the aforementioned basis. Amongst these particularly preferred embodiments, most preferred are those embodiments in which the concentration of the oxime compound is from about 10 to about 20% by weight of the solution.

In the third step of the process of this invention, the organic phase comprised of the oxime compound, the organic solvent, and the palladium is separated from the aqueous phase containing the remaining metals. In the preferred embodiments of the invention, conventional methods can be used to separate the phases through use of the immiscibility of the aqueous and organic phases. For example, since the oxime compound and organic solvent containing same are immiscible in the aqueous phase, these organic and aqueous phases can be separated using conventional immiscible phase separation techniques.

In the fourth step of the process of this invention, the organic phase is extracted with an aqueous ammonia solution. In the preferred embodiments of this invention, the aqueous ammonia solution is at least about 1 N in ammonia, and in the particularly preferred embodiments is from about 1 N to about 10 N in ammonia. Amongst these particularly preferred embodiments, most preferred are those embodiments in which the aqueous ammonia solution is from about 3 N to about 6 N in ammonia. For the recovery of palladium, use of the aqueous ammonia solution offers unique advantages, as it provides a method for readily isolating the palladium as the insoluble salt $Pd(NH_3)_2Cl_2$. Thus, the addition of hydrochloric acid to the palladium loaded aqueous ammonia solution precipitates palladium as the water insoluble salt $Pd(NH_3)_2Cl_2$. The isolation of this salt is common to many conventional methods for palladium recovery, and procedures for converting this salt to pure palladium metal are well known.

Process temperatures are not critical and can be varied widely. In general, process temperatures should be less than the boiling point of the oxime compound or any solvent which is employed. In the preferred embodiments of the invention, the process is conducted and a temperature of from about 10° C. to about 150° C., and in the particularly preferred embodiments from about 20° C. to about 100° C. Amongst these particularly preferred embodiments, most preferred are those embodiments in which the process temperature is from about 50° to about 80° C.

Process pressures are also not critical and can be varied widely. The process can be conducted at superatmospheric, atmospheric and sub-atmospheric pressure. For convenience the process is conducted at autogeneous pressure.

The process can be conducted in a batch, semicontinuous or continuous action. The present invention lends itself to operation in a single multi-stagecounter current extraction assembly and accordingly a further feature of the invention includes the use of a counter-current extraction assembly for the separation of palladium from aqueous solutions of one or more of the platinum group metals, rhodium, platinum, ruthenium, osminum, iridium, palladium and base metals as described above.

The following specific examples are presented to more particularly illustrate the invention.

EXAMPLE I

Preparation of (2-Methoxy-5-methyl)phenyl Pentadecyl Ketoxime

A mixture of 54 g (0.5 mol) p-cresol and 64.5 g (0.25 mol) palmitic acid was heated to 85°–90° C. for 3 hours, during which time a steady stream of $BF_3$ was added. The mixture was brought to 130° C. for an additional hour. After cooling, the reaction mixture was poured into ice water, with stirring. The product was collected by filtration, and then treated with 200 mL of boiling methanol to dissolve entrained p-cresol. The slurry was filtered, and the solid washed with cold methanol and dried to give (2-hydroxy-5-methyl)phenyl pentadecyl ketone in 84% yield; mp 54°–55° C.

IR (Nujol): 1640 cm$^{-1}$ (C=O);

NMR (CDC$_3$): δ 6.8–7.5 (3H), 2.95 (s, 3H), 2.2 (S, 3H), 1.2 (31H).

The above hydroxyphenyl ketone (50 g, 0.15 mol) and 42.6 g (0.30 mol) iodomethane were dissolved in 100 mL methylene chloride. This solution was stirred rapidly at 40° C. with a solution of 42 g (0.75 mol) potassium hydroxide and 4.7 g (0.015 mol) tetra-n-butylammonium bromide in 100 mL water. The reaction time was 5 hours. After cooling the reaction mixture, the phases were separated. The aqueous layer was extracted with 50 mL methylene chloride which was then added to the original methylene chloride layer. The combined organic layers were dried over anhydrous magnesium sulfate and concentrated under vacuum to an oil. The oil was taken up in petroleum ether and filtered to remove residual ammonium salt. The filtrate was again concentrated under vacuum to provide a light yellow oil, identified as (2-methoxy-5-methyl)phenyl pentadecyl ketone. The yield was 91%.

IR (thin film): 1660 cm$^{-1}$ (C=O);

NMR (CDCl$_3$): δ 6.8–7.1 (3H), 3.8 (s, 3H), OC$\underline{H}_3$), 2.75 (t, 2H), 2.2 (s, 3H, ArC$\underline{H}_3$), 1.2 (31H).

The above (2-methoxy-5-methyl)phenyl pentadecyl ketone was transformed into the corresponding ketoxime as follows. A solution of 1.94 g (0.028 mol) hydroxylamine hydrochloride in 50 mL methanol was neutralized, under a nitrogen atmosphere, by the addition of 1.57 g potassium hydroxide. After stirring 1 hour, the slurry was filtered to remove potassium chloride and 7.8 g (0.022 mol) of (2-methoxy-5-methyl)phenyl pentadecyl ketone was added to the filtrate. The resulting mixture was refluxed overnight. Methanol was removed under vacuum and the residue taken up in 100 mL methylene chloride which was then washed with 100 mL water. The methylene chloride layer was dried, and the solvent removed under vacuum to give 8.25 g (97% yield) of (2-methoxy-5-methyl)phenyl pentadecyl ketoxime, mp 51°–52° C. after recrystallization from ethanol-water. The infrared spectrum indicated the absence of the C=O bond of the starting material.

NMR (CDCl$_3$): δ 6.7–7.2 (m, 3H), 3.77 (s, 3H, OC$\underline{H}_3$), 2.75 (t, 2H), 2.3 (s, 3H, ArC$\underline{H}_3$), 1.2 (31H, aliphatic).

EXAMPLE II

Preparation of 2-Methoxy-5-nonylbenzophenone Oxime

A sample of 2-hydroxy-5-nonyl benzophenone (25 g, 0.077 mol) was dissolved in 100 mL methylene chloride. To this solution was added a solution of 20 g (0.5 mol) sodium hydroxide in 100 mL deionized water, followed by the addition of 22 g (0.154 mol) iodomethane and 2.5 g (0.006 mol) tetra-n-butylammonium bromide. The entire mixture was agitated with vigorous mechanical stirring for 1.5 hours at 40° C. The reaction mixture was allowed to cool, and the layers separated. The aqueous phase was extracted with 50 mL methylene chloride. The combined organic layers were dried over anhydrous magnesium sulfate and concentrated under vacuum. The residual oil was, taken up in petroleum ether, washed with water, dried over magnesium sulfate and again concentrated under vacuum to provide 22 g (85% yield) of 2-methoxy-5-nonyl benzophenone.

IR(film): 1660 cm$^{-1}$ (C=O);

NMR (CDCl$_3$): δ 6.8–7.7 (m, 8H), 3.7 (s, 3H, OC$\underline{H}_3$), 0.4–1.8 (m, 19H).

To 50 mL methanol (at 0° C. under nitrogen) was added 4.6 g (0.067 mol) hydroxylamine hydrochloride. Potassium hydroxide 3.75 g (0.067 mol) was then added and the mixture stirred 0.5 hours. Filtration of the resultant slurry was performed quickly, and the filtrate returned to the reaction flask. To the methanol solution of hydroxylamine was then added 2-methoxy-5-nonyl benzophenone, 22 g (0.065 mol), and the resulting mixture refluxed under nitrogen for 12 hours. The reaction mixture was cooled, and concentrated under vacuum to an oil. The oil was taken up in 75 mL methylene chloride and washed with an equal volume of water. The organic layer was then separated, dried over anhydrous magnesium sulfate and the volatiles removed under vacuum to give an oil (15 g, 65% yield) identified as 2-methoxy-5-nonyl benzophenone oxime. IR indicated the loss of C=O stretch at 1660 cm$^{-1}$.

NMR (CDCl$_3$): 6.8–7.7 (m, 8H), 3.75 (s, 3H, OCH$_3$; a singlet at δ 3.65 also appeared, which corresponds to the second geometrical isomer, the ratio of isomers being about 85:15), 0.4–1.8 (m, 19H).

EXAMPLE III

Preparation of 2-Isopropoxy-5-nonylbenzophenone Oxime

2-Isopropoxy-5-nonyl benzophenone was prepared as follows. To 25 g of 2-hydroxy-5-nonyl benzophenone in 100 mL CH$_2$Cl$_2$ was added 20 g NaOH in 100 mL water, followed by the addition of 48 g isopropyl bromide and 2.5 g tetra-n-butyl-ammonium bromide. The entire mixture was stirred vigorously at 40° C. for 3 days. The reaction mixture was worked up as described for the preparation of 2-methoxy-5-nonyl benzophenone (Example II) to give 16 g of yellow oil (57% yield), identified as the desired product.

IR(film): 1660 cm$^{-1}$ (C=O);

NMR (CDCl$_3$): δ 6.8–7.7 (m, 8H), 4.2 (m, 1H, (CH$_3$)$_2$C$\underline{H}$—), 0.2–1.5 (m, 25H).

To 150 mL methanol (at 0° C. and under nitrogen) was added 2.4 g hydroxylamine hydrochloride. Sodium hydroxide (2.0 g) was then added to the above solution and stirring continued for 1 hour. The slurry was quickly filtered to remove NaCl, and the filtrate was returned to the reaction flask. The above ketone, 12.0 g, was then added and the mixture stirred at room temperature overnight. The next day, an additional 5 g hydroxylamine hydrochloride was added, and the mixture refluxed for 12 hour more. The mixture was then cooled, the methanol removed under vacuum, and the residue taken up in 75 mL CH$_2$Cl$_2$. The methylene chloride solution was washed with 75 mL water, separated, dried (MgSO$_4$) and the volatiles removed under vacuum to provide 12.6 g (100% yield) of the desired 2-isopropoxy-5-nonyl benzophenone oxime (oil). IR(film) indicated complete loss of the C=O bond.

NMR (CDCl$_3$): δ 6.8–7.4 (m, 8H), 4.4 (m, 1H), 0.4–1.8 (m, 25H).

EXAMPLE IV

Preparation of 2-n-Pentoxy-5-nonylbenzophenone Oxime

A solution of 2-hydroxy-5-nonyl benzophenone, 15 g, in 100 mL methylene chloride was mixed with a solution of 9.25 g NaOH in 100 mL water. To this mixture was added 6.9 g n-pentyl bromide and 1.48 g tetra-n-butylammonium bromide. The whole mixture was then vigorously agitated overnight at 40° C. After cooling to room temperature with 50 mL CH$_2$Cl$_2$. The combined methylene chloride layers were concentrated to an oil, which was taken up in 100 mL petroleum ether and washed with 100 mL water. Finally, the organic layer was dried over anhydrous magnesium sulfate and the volatiles removed under vacuum to give 15 g (82% yield) of 2-n-pentoxy-5-nonyl benzophenone.

NMR (CDCl$_3$): δ 6.8–7.4 (m, 8H), 3.8 (t, 2H), 0.2–1.7 (m, 28H).

The above ketone was oximated as described in Examples 2 and 3 using 2.1 g hydroxylamine hydrochloride neutralized with 1.7 g potassium hydroxide in 125 mL methanol. The methanolic hydroxylamine solution was refluxed overnight with 6 g of the above ketone. Work-up provided 6.0 g (98% yield) of an oil identified as 2-pentoxy-5-nonyl benzophenone oxime. IR (film) indicated complete absence of the C=0 bond, and the presence of an OH stretch at about 3300 cm$^{-1}$.

NMR (CDCl$_3$): δ 6.8–7.3 (m, 8H), 3.8 (t, 2H), 0.8–1.6 (m, 28H).

EXAMPLE V

Preparation of 2-methoxy-5-nonylacetophenone

A solution of p-nonylphenol, 35 g, in 125 mL methylene chloride was mixed with a solution of 44.5 g KOH in 125 mL water. To this mixture was added 45 g iodomethane and 5.0 g tetra-n-butylammonium bromide. The whole mixture was vigorously stirred at 40° C. for one hour. After cooling to room temperature, the phases were separated and the aqueous phase extracted with 50 mL methylene chloride. The combined methylene chloride layers were concentrated to an oil which was taken up in 200 mL of petroleum ether and filtered to remove the residual phase transfer catalyst. Finally, the petroleum ether was removed under vacuum to give 31.1 g (84%) of p-nonylanisole.

NMR (CDCl$_3$): δ 6.6–7.3 (m, 4H), 3.75 (S, 3H), 0.5–1.8 (m, 19H).

A mixture of the above anisole (31 g) and glacial acetic acid (15 g) was heated to 70° C. for five hours, during which time a steady stream of BF$_3$ was added. After cooling the reaction mixture, it was dissolved in 200 mL methylene chloride and washed with 200 mL water. The organic layer was dried (MgSO$_4$) and the solvent was removed under vacuum to give 32.5 g of a red oil identified as a mixture of p-nonyl 2-methoxy-5-nonylacetophenone (major product) and 2-hydroxy-5-nonylacetophenone. To ensure complete conversion to the methoxyketone, the product mixture was re-alkylated by the phase transfer reaction described above. Work-up of the reaction mixture yielded 31.5 g (88%) of 2-methoxy-5-nonylacetophenone.

NMR (CDCl$_3$): δ 7.95 (d, 1H), 6.9 (apparent d, 2H), 3.8 (s, 3H), 2.5 (s, 3H), 0.5–1.8 (m, 19H); IR (thin film) 1675 cm$^{-1}$ (C=0).

The above methoxyketone was oximated as described in Example II, III, and IV using 10 g of hydroxylamine hydrochloride neutralized with 8.1 g potassium hydroxide in 250 mL methanol. The methanolic hydroxylamine solution was stirred overnight with 31.5 g of the ketone. Work-up yielded 28.5 g of an oil identified as 2-methoxy-5-nonylacetophenone oxime.

NMR (CDCl$_3$): δ 9.5 (b, 1H), 7.55 (d, 1H), 6.86 (apparent d, 2H), 3.8 (s, 3H), 2.25 (s, 3H), 0.5–1.9 (m, 19H).

IR (thin film) indicated complete absence of the C=0 bond.

EXAMPLE VI

Preparation of (2-Methoxy-5-methyl)phenyl Nonyl ketoxime

Decanoic acid (43 g) and p-cresol (54 g) were combined and heated to 80°–90° C. for 4–5 hours, while BF$_3$ was slowly bubbled into the solution. The solution was cooled and poured into ice-water. The oil was extracted with benzene and the benzene solution distilled to remove benzene and unreacted p-cresol. The distillation pot residue was washed with aqueous potassium carbonate to provide crude (2-hydroxy-5-methyl)-phenyl nonyl ketone.

NMR (CDCl$_3$): δ 7.6 (s, 1H, OH), 6.8–7.4 (3H, aromatic), 2.95 (t, 2H), 2.35 (s, 3H), 0.8–1.9 (m, 17H);

IR (film): 1640 cm$^{-1}$.

A solution of the above ketone (17.5 g) in 100 mL methylene chloride was mixed with a solution of 4.0 g NaOH in 100 mL water. To this mixture was added 9.9 g iodomethane and 1.2 g benzyl tri-n-butylammonium bromide. The whole mixture was stirred vigorously at room temperature overnight. After twelve hours an additional 23 g iodomethane was added and the reaction mixture heated to 40° C. with continued stirring for an additional four hours. After cooling to room temperature, the phases were separated and the aqueous phase extracted with 75 mL methylene chloride. The combined methylene chloride layers were dried over anhydrous magnesium sulfate and the solvent removed under vacuum to yield 13.6 g (74%) of (2-methoxy-5-methyl)phenyl nonyl ketone.

NMR (CDCl$_3$): δ 6.7–7.5 (m, 3H), 3.8 (s, 3H), 2.9 (t, 2H), 2.25 (s, 3H), 0.5–1.9 (m, 19H).

IR (thin film): 1670 cm$^{-1}$ (carbonyl).

The ketone was oximated as described earlier in Examples 2 and 3 using 3.5 g of hydroxylamine hydrochloride neutralized with 2.0 g sodium hydroxide in 50 mL methanol. The methanolic hydroxylamine solution was stirred overnight with 13.0 g of the ketone. The work-up yielded 13.9 g of a yellow oil that was vacuum distilled to yield 8.7 g of a compound identified as (2-methoxy-5-methyl)phenyl nonyl ketoxime (bp 154°–185° C./1 mm Hg).

NMR (CDCl$_3$): δ 6.8–7.2 (m, 3H), 3.8 (s, 3H), 2.7 (t, 2H), 2.2 (s, 3H), 0.5–1.8 (m, 17H).

EXAMPLE VII

An aqueous solution containing Pd(II), Fe(III), Ni(II), Cu(II), Mn(II) and Co(II) was prepared. The concentrations, as determined by atomic absorption spectroscopy, are given as the initial concentrations listed in Table 1. The pH of the solution was adjusted to 1 using hydrochloric acid. The aqueous metal solution was agitated with an equal volume of 5% (by weight) of (2-methoxy-5-methyl)phenyl pentadecyl ketoxime in kerosene (Kermac 627 a kerosene marketed and sold by Kerr-McGee) at room temperature for 1 hour. After separating the phases, the aqueous solution was again analyzed, the results being given in Table 1 as the final concentrations (average of three determinations). The results clearly demonstrate the high specificity of this oxime extractant for palladium over the base metals.

TABLE 1

| Metal | [Initial] ppm | [Final] ppm |
|---|---|---|
| $Pd^{2+}$ | 100 | 0.8 |
| $Fe^{3+}$ | 1910 | 1925 |
| $Ni^{2+}$ | 1895 | 1855 |
| $Cu^{2+}$ | 1970 | 1988 |
| $Mn^{2+}$ | 1910 | 1855 |
| $Co^{2+}$ | 1870 | 1850 |

EXAMPLE IX

The extraction of various metals alone using (2-methoxy-5-methyl)phenyl pentadecyl ketoxime was also tested under conditions similar to those described in Example VIII. The results are shown in Table 2. In these experiments, the aqueous phase contained only one metal. The results again show that palladium is readily extracted whereas the other metals are poorly extracted or not at all. Worthy of note is the lack of extraction of copper, which occurs readily with o-hydroxyphenyl oximes. Also noteworthy is the lack of extraction of the other platinum group metals, platinum and rhodium. The pH of the aqueous solutions were 1 unless noted otherwise.

TABLE 2

| Metal | [Initial] ppm | [Final] ppm |
|---|---|---|
| $Pd^{2+}$ | 960 | 9 |
| $Pt^{2+}$ (pH 3) | 966 | 970 |
| $Rh^{3+}$ | 1190 | 1135 |
| $Cu^{2+}$ | 1010 | 1000 |
| $Mn^{2+}$ | 1000 | 1020 |
| $Fe^{3+}$ | 1000 | 950 |
| $Al^{3+}$ (pH 3) | 985 | 960 |
| $Pb^{2+}$ | 1031 | 1046 |

EXAMPLE VIII

A solution of 5 weight percent (2-methoxy-5-methyl) phenyl pentadecyl ketoxime in kerosene (Kermac 627 a kerosene marketed and sold by Kerr-McGee Crop.) was prepared. A second solution was prepared by dissolving $K_2PdCl_4$ in dilute hydrochloric acid (pH=1). The concentration of palladium was 1028 ppm as determined by atomic absorption spectroscopy. The aqueous solution of $K_2PdCl_4$ was shaken with an equal volume of the first solution containing the oxime for 12 hours at room temperature. The two phases were separated and the aqueous phase analyzed for palladium content. The palladium concentration in the aqueous was found to be only 0.27 ppm, indicating greater than 99.9% extraction of the palladium present in the original aqueous solution. The example demonstrates that this oxime extractant can remove palladium values from aqueous solutions at pH 1 to the point where residual concentrations of palladium in the aqueous are less than 1 ppm.

EXAMPLE IX

A 5% by weight solution of 2-methoxy-5-nonyl benzophenone oxime in kerosene (Kermac 627) was prepared. This solution was agitated for 12 hours with an equal volume of an aqueous solution (pH 5) containing 930 ppm divalent palladium. After the extraction period, analysis of the aqueous phase indicated only 1 ppm palladium present, which represents the extraction of about 99.9% of the palladium present in the original aqueous phase. This example demonstrates the use of another preferred oxime extractant and also demonstrates that the extraction of palladium values is effective at pH 5.

EXAMPLE X

An aqueous solution containing 200 ppm Pd(II) at pH 4 was stirred with an equal volume of a 5 weight-/volume percent solution of 2-isopropoxy-5-nonylbenzophenone oxime in kerosene at room temperature for 10 minutes. The two layers were separated and the aqueous layer analyzed for palladium content. The analysis indicated 110 ppm Pd(II) in the aqueous phase or 45% uptake of the palladium by the oxime extractant in 10 minutes. This example demonstrates the use of another acceptable oxime extractant at pH 4.

EXAMPLE XI

A solution of 0.5 g of 2-pentoxy-5-nonyl benzophenone oxime was dissolved in 10 mL kerosene. This was stirred at room temperature for 10 minutes with an aqueous solution containing 334 ppm Pd(II) at pH 4. After the extraction period, the phases were separated and the aqueous phase analyzed for palladium content, which indicated 38 ppm Pd(II) present, or 89% uptake of palladium by the oxime extractant. The uptake of palladium in this example is significantly higher than that in Example 5, and suggests that branching at the carbon attached to the phenolic oxygen (the R group) is less preferred than a straight chain alkyl group attached to the oxygen or less preferred than R groups having branching sites remote from the phenolic oxygen.

EXAMPLE XII

A 5% by weight solution of 2-methoxy-5-nonylacetophenone oxime in kerosene (Fisher) was prepared. The solution was mixed for 12 hours with an equal volume of an aqueous solution (pH 3) containing 1900 ppm divalent palladium. After the extraction period, analysis of the aqueous phase indicated only 4.7 ppm palladium present, which represents the extraction of about 99.7% of the palladium present in the original phase. This example demonstrates the use of another preferred oxime extractant.

EXAMPLE XIII

A 5% by weight solution of (2-methoxy-5-methyl) phenyl nonylketoxime in kerosene (Fisher) was prepared. The solution was mixed for 12 hours with an equal volume of an aqueous solution (pH 1) containing 371 ppm divalent palladium. After the extraction period, analysis of the aqueous phase indicated only 0.6 ppm palladium present, which represents the extraction of about 99.8% of the palladium present in the original solution. This example demonstrates the use of another preferred oxime extractant.

EXAMPLE XIV

A solution of 0.5 g o-hexadecyloxyacetophenone oxime in 10 mL kerosene was rapidly stirred at 65°–70° C. with 10 mL of aqueous Pd(II) (concentration 450 ppm) at pH 4 for 10 minutes. After separating the layers, the concentration of Pd(II) in the aqueous phase was 150 ppm, representing a 67% uptake of Pd(II) by the oxime extractant under these conditions. Elevated temperatures were employed in this example because the oxime was not sufficiently soluble in kerosene at room temperature, which is more preferred.

EXAMPLE XV

Direct competition studies using solutions of Pd(II) and another metal were performed using (2-methoxy-5-methyl) phenyl pentadecyl ketoxime in kerosene. The pH in each case was 1. The concentration of the two metals in the aqueous phase were measured before and after the extraction. The results are set forth in Table 3 below.

TABLE 3

| Experiment No. | Initial Conc., ppm | Final Conc., ppm |
| --- | --- | --- |
| 1 | Pd(II) 1031 | Pd(II) >2 |
|   | Fe(III) 938 | Fe(III) 980 |
| 2 | Pd(II) 969 | Pd(II) 2.5 |
|   | Cu(II) 1035 | Cu(II) 1025 |
| 3 | Pd(II) 938 | Pd(II) none detected |
|   | Pt(IV) 790 | Pt(IV) 755 |
| 4 | Pd(II) 575 | Pd (II) 2.5 |
|   | Ni(II) 514 | Ni(II) 531 |

EXAMPLE XVI

The following example illustrates the stripping step (step 4) whereby palladium is stripped from the loaded oxime extractant using aqueous ammonia. A solution of Pd(II) (five volumes) at pH 1 and a concentration of 500 ppm was extracted with one volume of a kerosene solution of (2-methoxy-5-methyl)-phenyl pentadecyl ketoxime. After the extraction, the aqueous phase contained only 0.6 ppm $Pd^{2+}$, indicating that the loaded organic phase contained 2500 ppm palladium. The palladium-loaded organic phase was then stripped with an equal volume of 5 M $NH_4OH$ at 70° C. for one hour. The concentration of palladium in the aqueous ammonia phase was found to be 2300 ppm after the stripping operation. Repeating the stripping of the same organic phase with another equal volume of fresh ammonia solution removed the remaining 200 ppm palladium from the organic phase. Thus, essentially all the palladium was removed from the oxime extractant with two sequential strippings with aqueous ammonia. Acidifying the palladium rich ammonia solution with HCl resulted in the precipitation of a yellow solid, identified by its infrared spectrum as $Pd(NH_3)_2Cl_2$.

COMPARATIVE EXAMPLE 1

A 5% by weight solution of (2-methoxy-5-nonyl) benzophenone oxime-O-methyl ether in kerosene was prepared. This solution was mixed for 12 hours with an equal volume of an aqueous solution (pH 3) containing 294 ppm Pd(II). After the extraction period, analysis of the aqueous phase indicated 274 ppm palladium present, representing an extraction of only 6.8% of the Pd(II) present in the original solution. This example demonstrates that alkylation of the oxime oxygen greatly reduces the ability of the oxime compound to effectively extract palladium.

What is claimed is:

1. A process for the separation and purification of palladium which is present in a platinum group metal-containing aqueous solution, said process comprising the steps of:

(a) adjusting the pH of the solution to 5 or less;

(b) contacting said acidic solution with one or more oxime compounds of the formula:

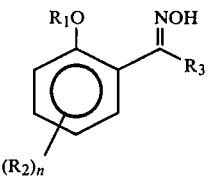

or a composition comprised of one or more of said compounds dissolved in an organic solvent, wherein:

n is an integer of from 1 to 4;

$R_1$ is alkyl, cycloalkyl, or aralkyl; and $R_2$ is nitro, halogen, hydrogen or substituted or unsubstituted alkyl, alkoxy, aryloxy, cycloalkyl, aryl, aralkyl or alkaryl wherein permissible substituents are those which are inert to the process conditions; and $R_3$ is alkyl, aryl, alkaryl, cycloalkyl, or aralkyl either unsubstituted or substituted with one or more of the above referenced permissible substituents; and (c) removing from contact with said aqueous acidic solution the organic phase containing all or a part of the palladium originally present in said solution and said oxime compound; and (d) extracting said palladium from the organic solvent with an aqueous ammonia solution.

2. A process according to claim 1 wherein n is 1 or 2.

3. A process according to claim 2 wherein n is 1.

4. A process according to claim 1 wherein $R_1$ is straight chain alkyl having from 1 to about 6 carbon atoms.

5. A process according to claim 4 wherein $R_1$ is alkyl from 1 to about 3 carbon.

6. A process according to claim 5 wherein $R_1$ is methyl.

7. A process according to claim 1 wherein $R_2$ and $R_3$ are the same or different and are unsubstituted alkyl, aralkyl, aryl or alkaryl with the proviso that the $R_2$ substituent is substituted at the meta and/or para positions relative to the oximino function and with the further proviso that $R_2$ and $R_3$ together contain a total of from about 15 to about 30 carbon atoms.

8. A process according to claim 7 wherein $R_2$ is straight chain alkyl having from 1 to about 12 carbon atoms substituted at the meta position relative to the oximino function.

9. A process according to claim 8 wherein $R_2$ is alkyl having from about 8 to about 10 carbon atoms.

10. A process according to claim 7 wherein $R_3$ is straight chain alkyl having from about 12 to about 25 carbon atoms and aryl.

11. A process according to claim 10 wherein $R_3$ is aryl.

12. A process according to claim 11 wherein $R_3$ is phenyl.

13. A process according to claim 10 wherein $R_3$ is straight chain alkyl having from about 12 to 29 carbon atoms.

14. A process according to claim 1 wherein;

n is 1 or 2;

$R_1$ is straight chain alkyl having from 1 to about 6 carbon atoms; and $R_2$ and $R_3$ are the same or different and are unsubstituted alkyl, aralkyl, aryl or alkaryl with the proviso that the $R_2$ substituent is substituted at the meta and/or para position relative to the oximino function and with the further proviso that $R_2$ and $R_3$ together contain a total of from about 15 to about 30 carbon atoms.

15. A process according to claim 14 wherein:
n is 1;
$R_1$ is straight chain alkyl having from 1 to about 3 carbon atoms;
$R_2$ is straight chain alkyl having from 1 to about 12 carbon atoms substituted at the meta position relative to the oximino function; and
$R_3$ straight chain alkyl having from 12 to about 25 carbon atoms and aryl.

16. A process according to claim 15 wherein $R_1$ is methyl.

17. A process according to claim 16 wherein $R_2$ is nonyl.

18. A process according to claim 17 wherein $R_3$ is straight chain alkyl having from about 12 to about 25 carbon atoms.

19. A process according to claim 17 wherein $R_3$ is aryl.

20. A process according to claim 15 wherein:
$R_1$ and $R_2$ are methyl; and
$R_3$ is straight chain alkyl having from about 12 to about 25 carbon atoms.

21. A process according to claim 15 wherein said one or more compounds are selected from the group consisting of (2-methoxy-5-methyl) phenyl pentadecyl ketoxime and 2-methoxy-5-nonyl benzophenone oxime.

22. A process according to claim 1 wherein said pH is from about −0.5 to about 5.

23. A process according to claim 1 wherein said pH is from about 0 to about 3.

24. A process according to claim 1 wherein said pH is from about 0 to about 1.

25. A process according to claim 1 wherein said acidified platinum group metal containing solution is contacted with a solution of a one or more of the said oxime compounds dissolved in an organic solvent.

26. A process for the separation and purification of the palladium which is present in platinum group metal-containing solutions which comprises the steps of
a. adjusting the platinum group metal-containing solution to give a pH within the range of from about −0.5 to about 5;
b. contacting by means of a solvent extraction technique, the acidic solution with an oxime compound of the formula:

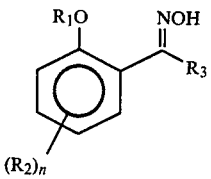

or a composition composed of one or more of said compounds dissolved in an organic solvent, wherein:
n is an integer of from 1 to 4;
$R_1$ is alkyl, cycloalkyl, or aralkyl;
$R_2$ is nitro, halogen, hydrogen or substituted or unsubstituted alkoxy, aryloxy, cycloalkyl, aryl, alkoxy, aryloxy, aralkyl or alkaryl wherein permissible substituents are those which are inert to the process conditions; and
$R_3$ is alkyl, aryl, cycloalkyl, alkaryl, or aralkyl either unsubstituted or substituted with one or more of the above referenced permissible substitutents with the proviso that $R_2$ and $R_3$ together include a total of 7 or more carbon atoms;
c. removing from contact with the acidic solution the organic phase containing all or a part of the palladium originally present in said solution and said oxime compounds; and
d. extracting said palladium from said organic phase with an aqueous ammonia solution.

27. A process according to claim 26 carried out in a multi-stage counter-current solvent extraction apparatus.

* * * * *